US007852479B2

(12) United States Patent  
Johnson

(10) Patent No.: US 7,852,479 B2
(45) Date of Patent: Dec. 14, 2010

(54) APPARATUS AND METHOD FOR MEASURING THE FLUORESCENCE OF LARGE MULTI-CELLULAR ORGANISMS

(75) Inventor: Paul E. Johnson, Laramie, WY (US)

(73) Assignee: University of Wyoming, Laramie, WY (US)

( * ) Notice: Subject to any disclaimer, the term of this patent is extended or adjusted under 35 U.S.C. 154(b) by 409 days.

(21) Appl. No.: 11/985,038

(22) Filed: Nov. 13, 2007

(65) Prior Publication Data

US 2008/0129998 A1    Jun. 5, 2008

Related U.S. Application Data

(60) Provisional application No. 60/858,646, filed on Nov. 13, 2006, provisional application No. 60/920,111, filed on Mar. 26, 2007.

(51) Int. Cl.
*G01N 21/25* (2006.01)
(52) U.S. Cl. .................................... 356/417
(58) Field of Classification Search ............... 356/317, 356/417, 72–73
See application file for complete search history.

(56) References Cited

U.S. PATENT DOCUMENTS

| 3,929,411 | A | 12/1975 | Takano |
| 6,309,886 | B1 | 10/2001 | Johnson |
| 6,765,656 | B2 | 7/2004 | Johnson |
| 7,161,665 | B2 | 1/2007 | Johnson |
| 2001/0036668 | A1* | 11/2001 | Furlong et al. ............ 436/172 |
| 2002/0003625 | A1 | 1/2002 | Hansen |
| 2002/0033939 | A1* | 3/2002 | Hansen ..................... 356/73 |
| 2003/0148531 | A1* | 8/2003 | Hatcher et al. ............ 422/73 |
| 2005/0036139 | A1 | 2/2005 | Johnson |
| 2006/0101528 | A1 | 5/2006 | Demeneix |
| 2007/0159627 | A1 | 7/2007 | Johnson |

FOREIGN PATENT DOCUMENTS

| DE | 4315928 | 12/1994 |
| EP | 0333560 | 9/1989 |
| EP | 0435111 | 7/1991 |
| EP | 0475533 | 3/1992 |
| WO | WO 9833054 | 10/1998 |

OTHER PUBLICATIONS

U.S. Appl. No. 10/516,134, Sep. 12, 2005, Demeneix et al.

* cited by examiner

*Primary Examiner*—Kara E Geisel
(74) *Attorney, Agent, or Firm*—Jennifer L. Bales; Macheledt Bales LLP

(57) ABSTRACT

Apparatus and methods for measuring the fluorescence of large multi-cellular organisms in a sample of liquid includes a pumping mechanism, a fluorescence measuring device, a method of analyzing the measurements, and optionally, a sorting mechanism. The pumping mechanism transfers large multi-cellular organisms from a reservoir through a fluorescence-measuring device causing minimum physical damage and/or stress. The pressure differential driving the organisms from a sample container/reservoir through the measuring device can be derived from gravity, air pressure, or liquid pressure, or some combination of the three. The fluorescence can be measured in a cytometer using a light detector or imager. Generally the detection element will include a filter, isolating the wavelength of fluorescent emission. The illumination may be provided by a laser or by an LED, combined with the use of dichroic mirrors to allow multiple wavelength simultaneous illumination.

17 Claims, 9 Drawing Sheets

APPARATUS AND METHOD FOR MEASURING THE FLUORESCENCE OF LARGE MULTI-CELLULAR ORGANISMS

This patent application claims priority to U.S. Provisional Application Ser. Nos. 60/858,646, filed Nov. 13, 2006 and 60/920,111, filed Mar. 26, 2007.

BACKGROUND OF THE INVENTION

1. Field of the Invention

The present invention relates to apparatus and methods for making fluorescence measurements and sorting large multi-cellular organisms in a flowing liquid.

2. Background

WatchFrog (Paris, France) has developed a technique for sensitively testing for pollutants in the environment and for pharmaceutical testing. *Xenopus* tadpoles "light up" (exhibit fluorescence) in response to a pollutant (or drug), and can indicate the presence of several chemical species at the same time. This is described in publicly available literature (for example, Turque et al. 2005) and in US Patent Application 20060101528 (Demeneix and Turque) on transgenic *Xenopus*, and is summarized below:

The basic principle involves creating genetic constructions that enable a GFP (Green Fluorescent Protein) to be expressed in response to the physiological action of whatever type of molecules a customer may be interested in. This 'molecular dosimeter' is then incorporated in a *Xenopus* larva, thereby taking into account all the biochemical regulations that can respond in vivo to the sample being tested.

For example, if an endocrine disrupter is present, it will activate the response element of various hormones, such as estrogen or thyroid hormone, triggering the synthesis of fluorescent proteins. The fluorescence is visible through the transparency of the organism, and can therefore be detected and quantified without sacrificing the animal. The larvae simply need to be placed in the liquid sample to implement the test. The genetic constructions can be altered as required to produce a tailor-made range of tests to respond to various disruptive or pharmacological effects.

This test methodology combines the advantages of in vivo with the flexibility of in vitro. It rapidly and simply furnishes accurate information of high sensitivity and specificity, together with low cost, economic use of material, and the potential for automation.

*Xenopus* (the choice of species) has a complete immune system, as well as a more complex heart and circulatory system. In addition, in terms of endocrine physiology, the conservation of biochemical mechanisms between *Xenopus* and humans has been demonstrated and proved. *Xenopus* is an investigated and recognized model in the research world.

In addition, *Xenopus* allows a number of pharmaceutical applications. For example: *Xenopus* is again relevant in that it very rapidly develops a vascular system and a complex central nervous system in the course of its growth. Thus we are able to develop target-models to test new molecules of angiogenic or neurological interest.

Also known in the art are various methods of detecting particles. For example, U.S. Pat. No. 6,765,656 to the present inventor teaches a fountain flow cytometer, wherein a sample of fluorescently tagged cells flows up a tube toward a digital CCD or CMOS camera and fore-optics. See FIG. 1 (Prior Art). The cells are illuminated in the focal plane by a laser through a transparent end element. When the cell(s) pass through the digital camera focal plane, they are imaged by the camera and a lens assembly, through a transparent window and a filter that isolates the wavelength of fluorescent emission. The fluid in which the cells are suspended then passes by the window ad out the drain tube.

FIG. 1 (Prior Art) shows a schematic diagram of the epifluorescent Fountain Flow™ Cytometer 100 as used in this study. A Sample 102 of fluorescent organisms flows through the flow cell 104 toward the digital camera 106 and fore-optics 108. The cells are illuminated in the focal plane 110 by a laser 112. Then the cell(s) pass through the CCD camera focal plane and they are imaged by the CCD camera and lens assembly through the transparent flow cell window, using a filter 114 that isolates the wavelength of fluorescence emission. The fluid in which the cells are suspended then passes by the window 118 and effluent 120 flows out the flow cell drain tube 116 (in the path indicated by the arrows).

A flow block may be used as flow cell 104, as shown in FIG. 2 (Prior Art) wherein the sample 102 enters the flow block through entrance tube 202 via input tubing 208, is forced up and under an imaging window 118, and flows back down to exit through drain tube 116 and out effluent exit tubing 206.

FIG. 2 (Prior Art) shows a schematic drawing of an aluminum flow block used as flow cell 104 with the device in FIG. 1. The sample 102 enters the flow block 104 through a flexible tubing (Tygon™ or the like) input tubing 208 connected to a stainless steel entrance tube 202 and exists through stainless steel drain tube 116 to effluent exit tubing 206. Two vertical 8-mm holes have been drilled into the aluminum flow block: an entrance hole 210 and an exit hole 214. As the sample flows up the internal entrance hole 210, it passes through the focal plane 110 of the digital (e.g. CCD or CMOS) camera 106. This hole 210 is generally painted black to reduce scattered light. A Teflon tape gasket 216 is sandwiched between the aluminum flow block and a circular BK7 window 118, and tightly held with a screw-on brass cap 218. The gasket is cut to allow the sample to be viewed through window 118. Sample 102 then passes down exit hole 214 to drain tube 116. LED illumination may be used as shown in FIG. 3 (Prior Art).

FIG. 3 (Prior Art) shows a schematic diagram of an LED-illuminated epifluorescent Fountain Flow Cytometer 300. A sample of fluorescently tagged cells flows through the flow cell 104 toward the digital camera 106 and fore-optics 108. The cells are illuminated in the focal plane by an LED 302. When the cell(s) pass through the CMOS camera focal plane 110, they are imaged by the camera and lens assembly 108 through the transparent flow cell window 118, and a filter (not shown) that isolates the wavelength of fluorescence emission. The fluid in which the cells are suspended then passes by the window 118 and out the flow cell drain tube 116. (Note: in the current embodiment a peristaltic pump is not used.)

BACKGROUND REFERENCES

1. Demeneix, B and Turque, N. Transgenic clawed frog embryos and use thereof as detectors of endocrine disrupters in the environment. US Patent Application 20060101528.
2. Johnson P E, Votaw A S, Deromedi, A J. Biodetection with flow cytometry: better, faster, cheaper. In Biodetection Technologies, vol. 1. Brookline, Mass.: Knowledge Press; 2002; p 71-83.
3. Johnson P E. Apparatus and methods for high throughput analysis of samples in a translucent flowing liquid. U.S. Pat. No. 6,765,656; 2004.
4. Johnson, P E, Deromedi, A J, Lebaron, P, Catala, P., and Cash, J. Rapid detection and enumeration of *Escherichia coli* in aqueous samples using Fountain Flow Cytometry, in press, Cytometry Part A, 69A, 1212-1221, 2006.

5. Johnson, P E, Deromedi, A J, Lebaron, P, Catala, P, Havens, C, and Pougnard, C. High throughput, real-time detection of *Naegleria lovaniensis* in natural river water using LED-illuminated Fountain Flow Cytometry, 103(3), 700-720 J Appl Microbiol, 2007.
6. Johnson P E. Method and system for counting particles in a laminar flow with an imaging device. U.S. patent application Ser. No. 11/328,033; 2006.
7. www.watchfrog.fr. Accessed Nov. 11, 2006.
8. Turque, N., Palmier, K., Le Mével, S., Alliot, C. and Demeneix, B. A. A Rapid, Physiologic Protocol for Testing Transcriptional Effects of Thyroid-Disrupting Agents in Premetamorphic *Xenopus* Tadpoles. *Environmental Health Perspectives*, 113, Number 11. November 2005.

SUMMARY

An invention is described which allows fluorescence measurements of an aqueous sample containing large (~1-5 mm wide) multi-cellular organisms in real time. The system includes at least a pumping subsystem, a fluorescence measurement subsystem, and a unit for processing the measurements. In addition, the system could include a sorting unit that would sort the organisms into containers according to their fluorescence, for further analysis. One constraint on the pumping unit is that it must be non-destructive to the organisms in the sample. The pumping method in this invention is based on air pressure and/or gravity and is relatively stress free to the organisms being pumped. The preferred technology for measuring organism fluorescence, presented here, is the fountain flow cytometry technique summarized above and described in detail in U.S. Pat. No. 6,765,656, combined with LED illumination and a digital imager.

Apparatus for pumping a fluid sample containing multi-cellular organisms from a sample reservoir through a fluorescence measuring device to a waste container without passing the organisms through a pump, includes a sample reservoir containing the sample, means for selectively applying a pressure differential between the sample reservoir and the waste container, a first outlet for connecting the sample reservoir to a fluorescence measuring device, a waste container, and a second outlet for connecting the fluorescence measuring device to the waste container. When the pressure differential is applied, a portion of the sample flows from the sample reservoir, through the first outlet, through the fluorescence measuring device, and through the second outlet to the waste container, and the portion of the sample never passes through a pump.

The multi-cellular organisms might be from 0.1 mm to 3 cm long, for example *Xenopus* tadpoles.

The means for selectively applying a pressure differential can be an air pump connected to the sample reservoir for raising the pressure in the sample reservoir.

As an alternative, the means for selectively applying a pressure differential uses gravity. The means for selectively applying a pressure differential raises the fluid level in the sample reservoir to a first level, the first level higher than the fluid level in the waste container. As a feature, this embodiment may also include the ability to pass the sample portion back from the waste container to the sample reservoir for re-measuring. This is accomplished by lowering the fluid level in the sample reservoir to a second level, the second level below the fluid level in the waste container. A valve allows the recycled sample portion to flow from the waste container to the sample reservoir.

Generally the second embodiment includes a screen in the sample reservoir configured to contain the organisms below the second level.

In some embodiments, the sample reservoir is configured to have a low area narrower than the sample reservoir cross-section into which the organisms can settle. The first outlet might then include a pipe extending into the low area to siphon the organisms. The pipe can have a bent end to reach into this low area.

Preferably the pressure differential is sufficient to achieve a sample flow rate of about 140 ml/minute. Generally the fluorescent measuring device includes a detection element for measuring light intensity within the sample. A feature is a mechanism for sorting organisms according to the measured light intensity after they exit the fluorescent measuring device.

DETAILED DESCRIPTION OF THE PREFERRED EMBODIMENT

The following reference numbers are used in the figures:

| | |
|---|---|
| 100 | Cytometer |
| 102 | Sample |
| 104 | Flow cell |
| 106 | Digital camera |
| 108 | Optics |
| 110 | Focal plane |
| 112 | Laser |
| 114 | Filter |
| 116 | Drain tube |
| 118 | Window |
| 120 | Effluent |
| 202 | Entrance tube |
| 206 | Effluent exit tubing |
| 208 | Tubing from pump |
| 210 | Entrance hole |
| 214 | Exit hole |
| 216 | Gasket |
| 218 | Screw on cap |
| 300 | LED cytometer |
| 302 | LED |
| 402 | Sampling reservoir |
| 404 | Air pipe |
| 406 | Sample pipe |

-continued

| | |
|---|---|
| 408 | Bent end |
| 410 | Variac (variable voltage transformer) |
| 412 | Air pump |
| 414 | Tubing to sample reservoir |
| 416 | Tubing to flow cell |
| 418 | Viewing area |
| 420 | Tubing to waste container |
| 422 | Waste container |
| 502 | Valve |
| 504, 506 | Bins |
| 508 | Measuring equipment |
| 602 | Pumped air |
| 604 | Sample introduction valve |
| 606 | Sample introduction funnel |
| 702, 704, 706 | Reservoir configuration |
| 708 | Bent pipe |
| 800 | Gravity embodiment |
| 802 | Sample introduction funnel |
| 804 | Sample |
| 806 | First cylinder |
| 808 | First cylinder level maintaining outflow |
| 810 | First cylinder water fill valve |
| 812 | Drain, first cylinder to second cylinder |
| 814 | Valve to first cylinder from flow cell |
| 816 | Sample path, first cylinder to second cylinder |
| 818 | Sample path, flow cell to first cylinder |
| 820 | Drain, second cylinder to flow cell |
| 822 | Drain tube |
| 824 | Drain valve |
| 826 | Second cylinder |
| 828 | Second cylinder water fill valve |
| 830 | Second cylinder level maintaining outflow |
| 832 | Second cylinder level maintaining valve |
| 834 | Second cylinder sample input valve |
| 836, 838 | Second cylinder fill levels |
| 840 | Second cylinder sample volume |
| 842 | Second cylinder screen |
| 846 | First cylinder screen |

Figure 5:
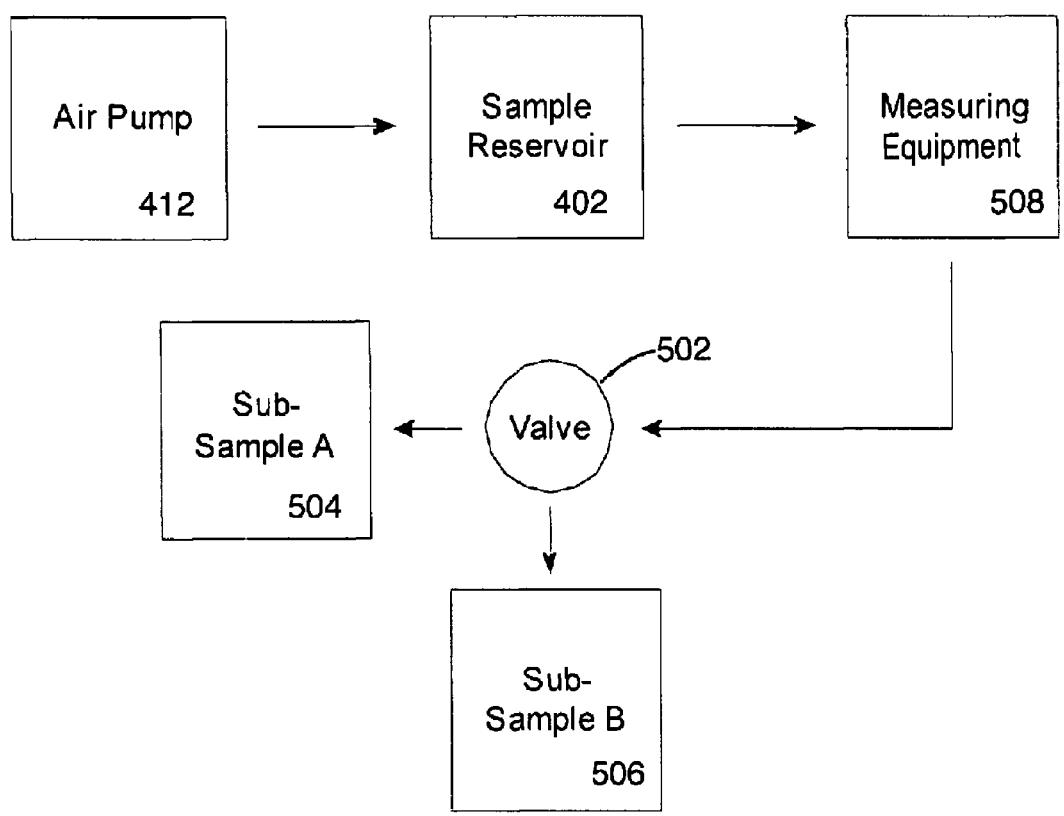
FIG. 5 is a block diagram illustrating the process performed by the present invention.
Figure 6A:
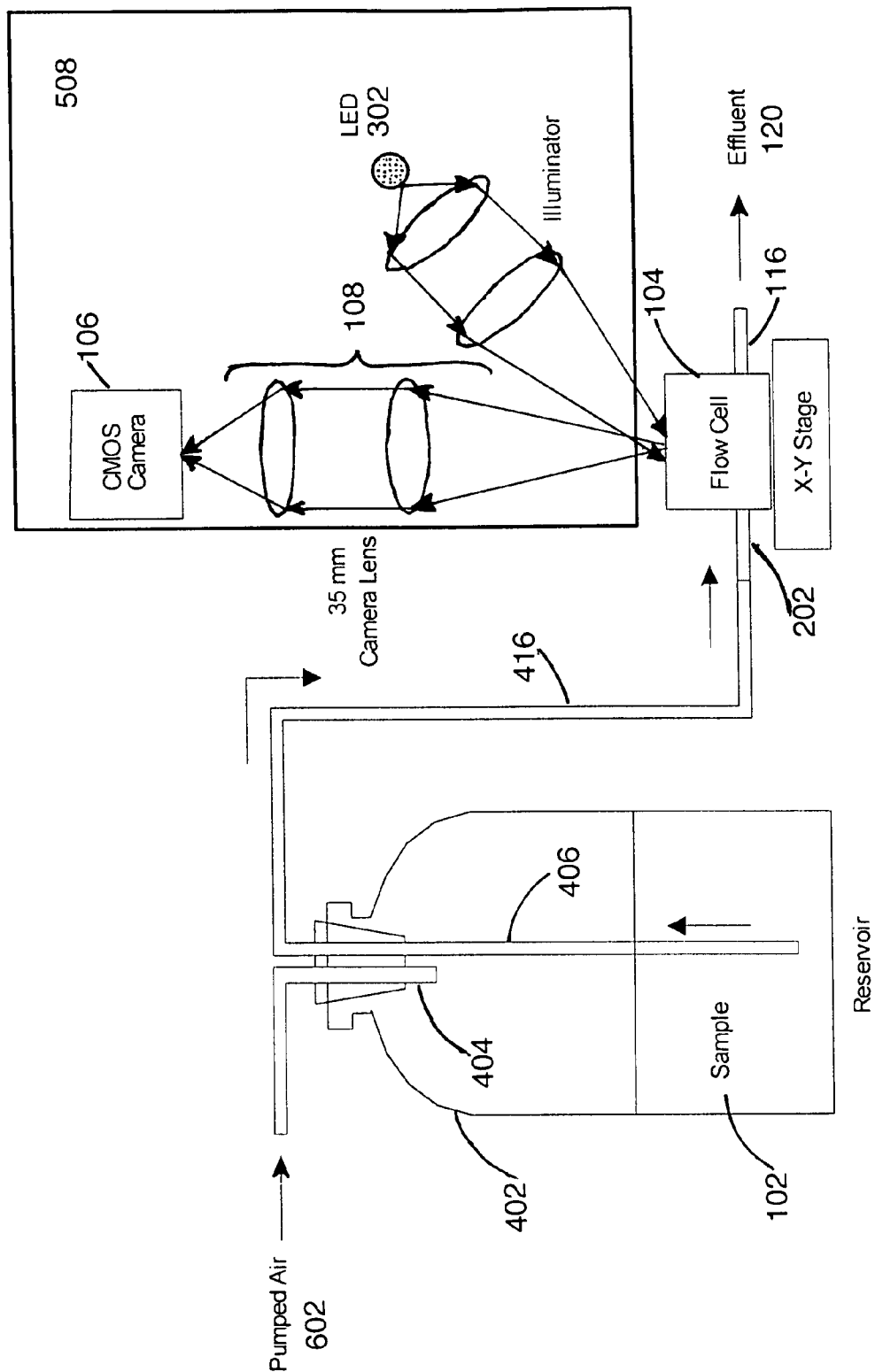
FIG. 6A is a schematic diagram illustrating the pumping system of the present invention used in a fountain flow configuration.
Figure 6B:
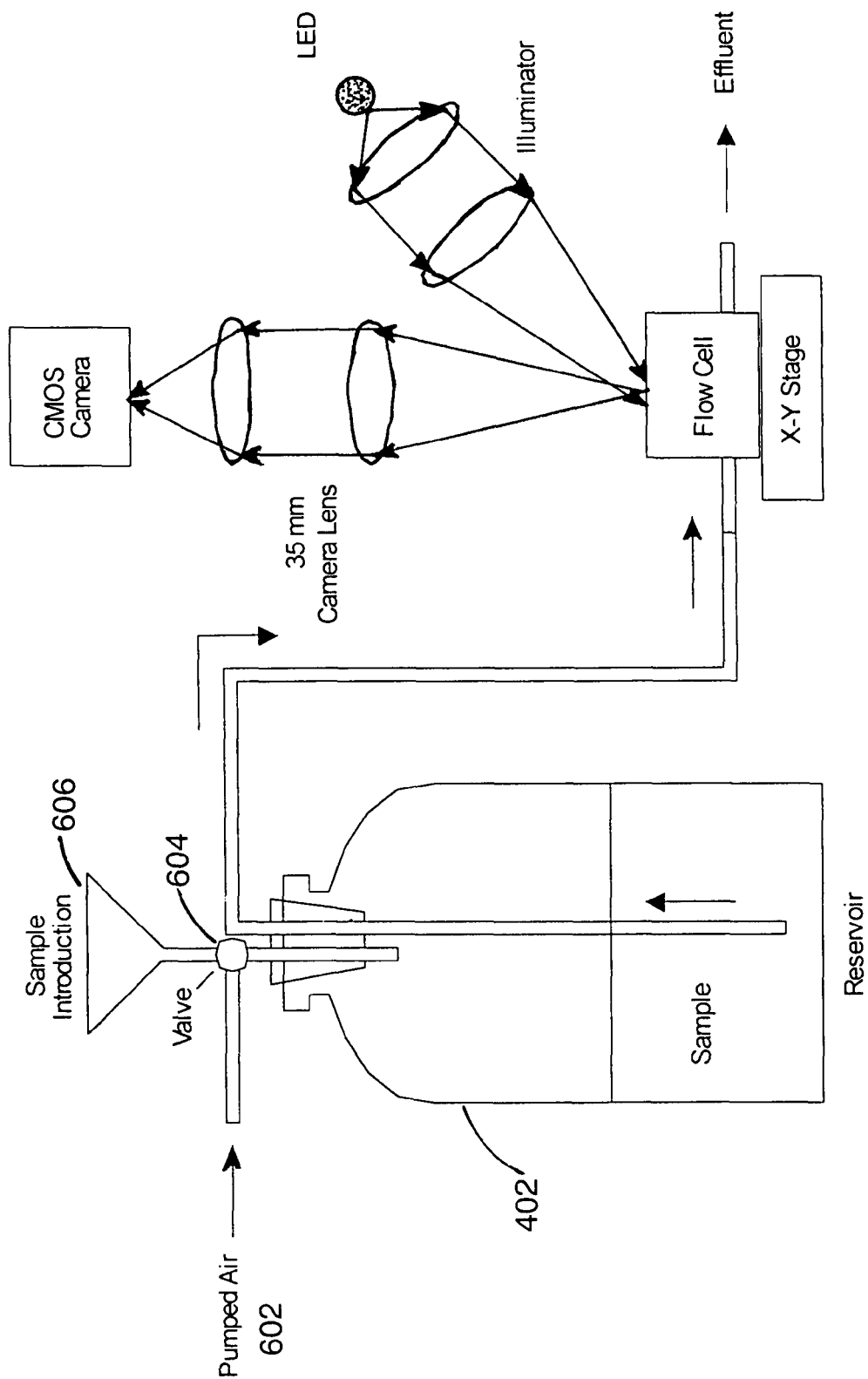
FIG. 6B is a schematic diagram of an embodiment of the present invention showing sample reservoir with a sample introduction unit.
Figure 7:
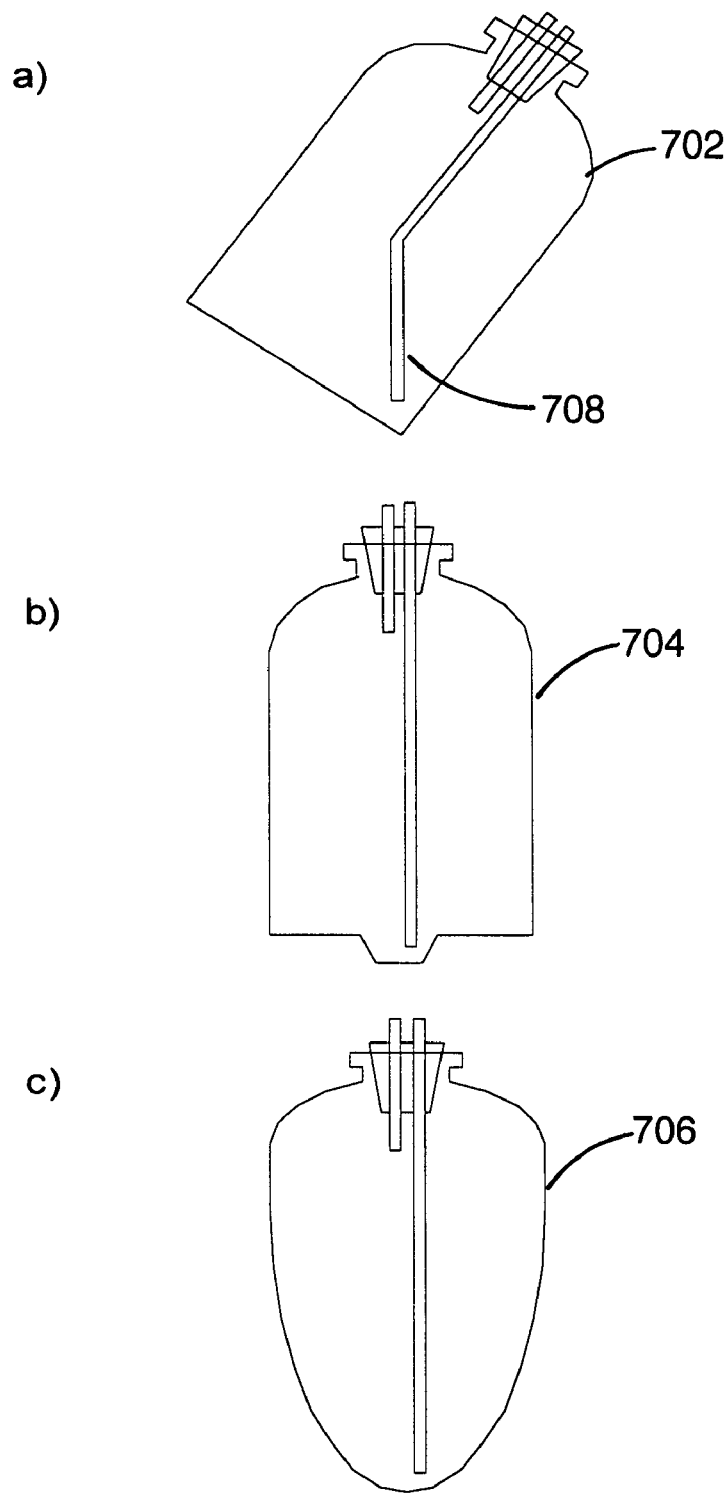
FIGS. 7A-7C illustrate possible reservoir configurations for use with the present invention.

The present invention includes apparatus and methods for measuring the fluorescence of large multi-cellular organisms in a sample of liquid. The apparatus includes two pumping mechanisms. The first, shown in FIG. 4, uses air pressure and gravity, while a second, shown in FIG. 8, uses gravity alone. A fluorescence measuring device is shown in FIG. 6A, and a mechanism for introducing a sample is shown in FIG. 6B. A method of analyzing the measurements, including an optional sorting mechanism is shown in FIG. 5. FIGS. 7A-C show examples of reservoir vessels suited to the present invention.

The pumping mechanism embodiments transfer large multi-cellular organisms from a reservoir through a fluorescence-measuring device causing minimum physical damage and/or stress. The pressure differential driving the organisms from a sample container/reservoir through the measuring device can be derived from gravity, air pressure, liquid pressure, or some combination of the three. The fluorescence can be measured in a fountain flow cytometer using a light detector or imager, including: CMOS detector, a charge-coupled device, or any other imaging or light detecting unit. Generally the detection element will include a filter, isolating the wavelength of fluorescent emission. The illumination may be provided by a laser or by an LED, combined with the use of dichroic mirrors to allow multiple wavelengths simultaneous illumination. In addition, an LED will typically be used with a filter to isolate the optimum excitation wavelength while blocking scattered/reflected LED light from the detection element (but not the fluorescent emission).

In the preferred (and reduced to practice) embodiment, the organism to be tested is *Xenopus*, either wild type or genetically modified. A specific embodiment of the present invention is described in detail below.

1. Pump

Figure 1:
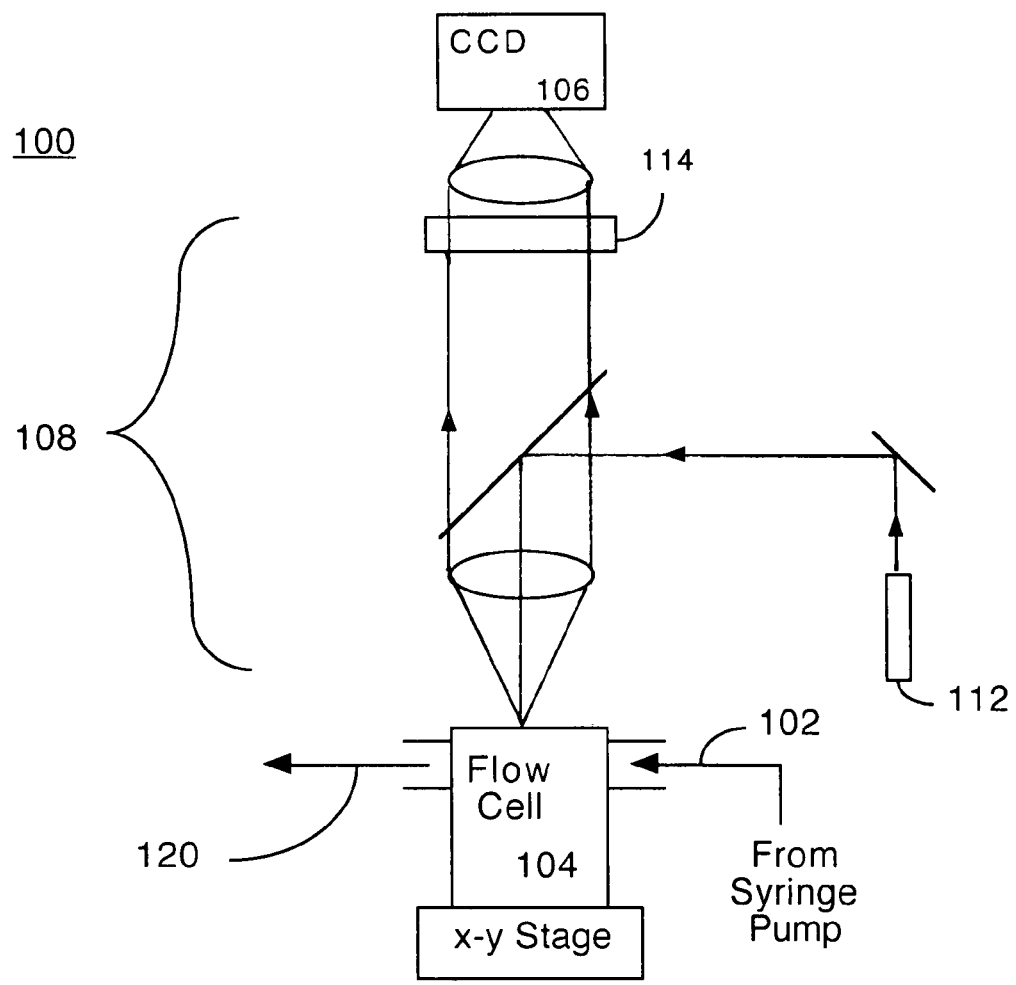
FIG. 1 (Prior Art) shows a schematic diagram of an epifluorescent fountain flow cytometer.
Figure 2:
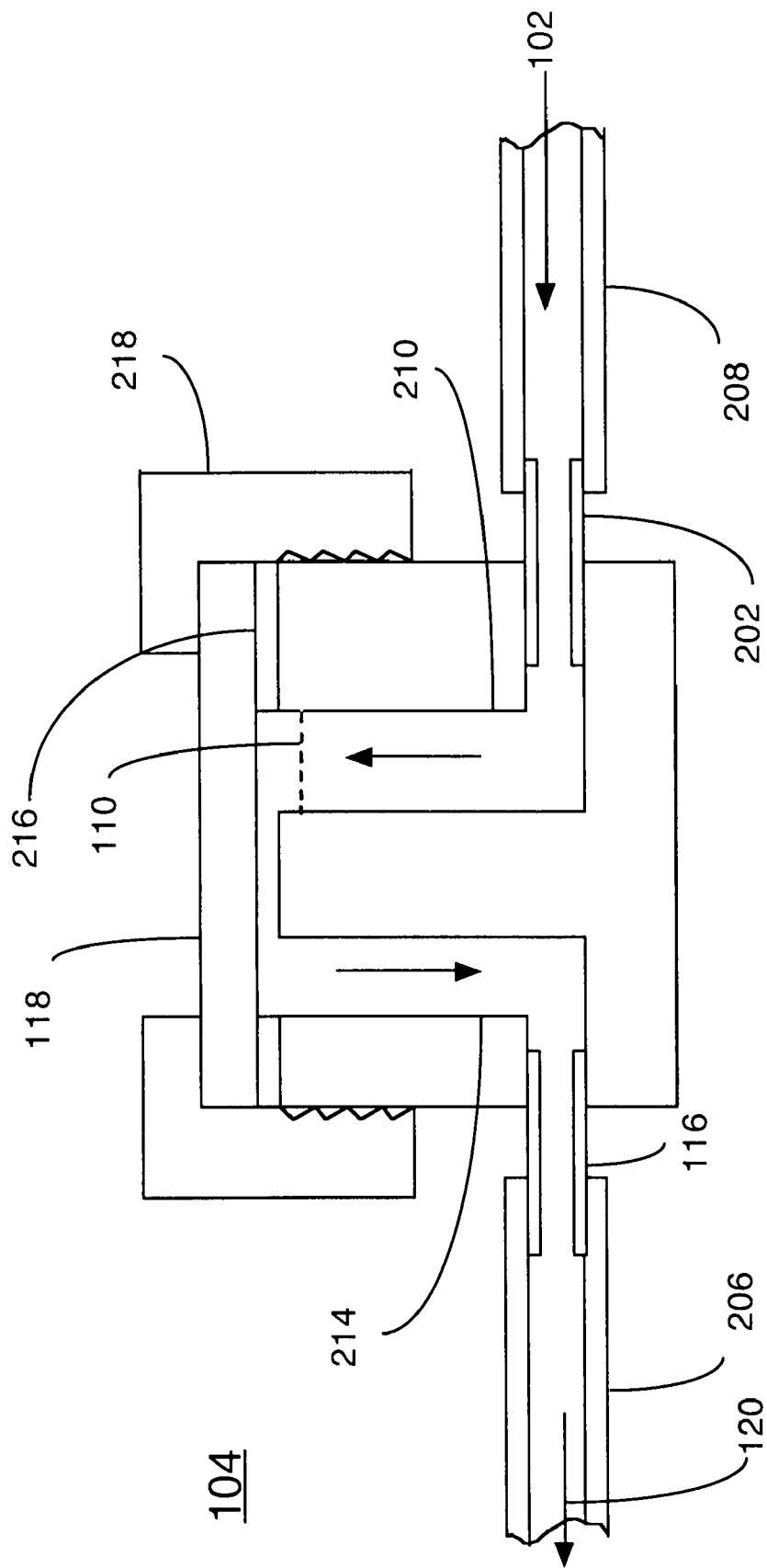
FIG. 2 (Prior Art) shows an aluminum flow block tube used with the device of FIG. 1.
Figure 3:
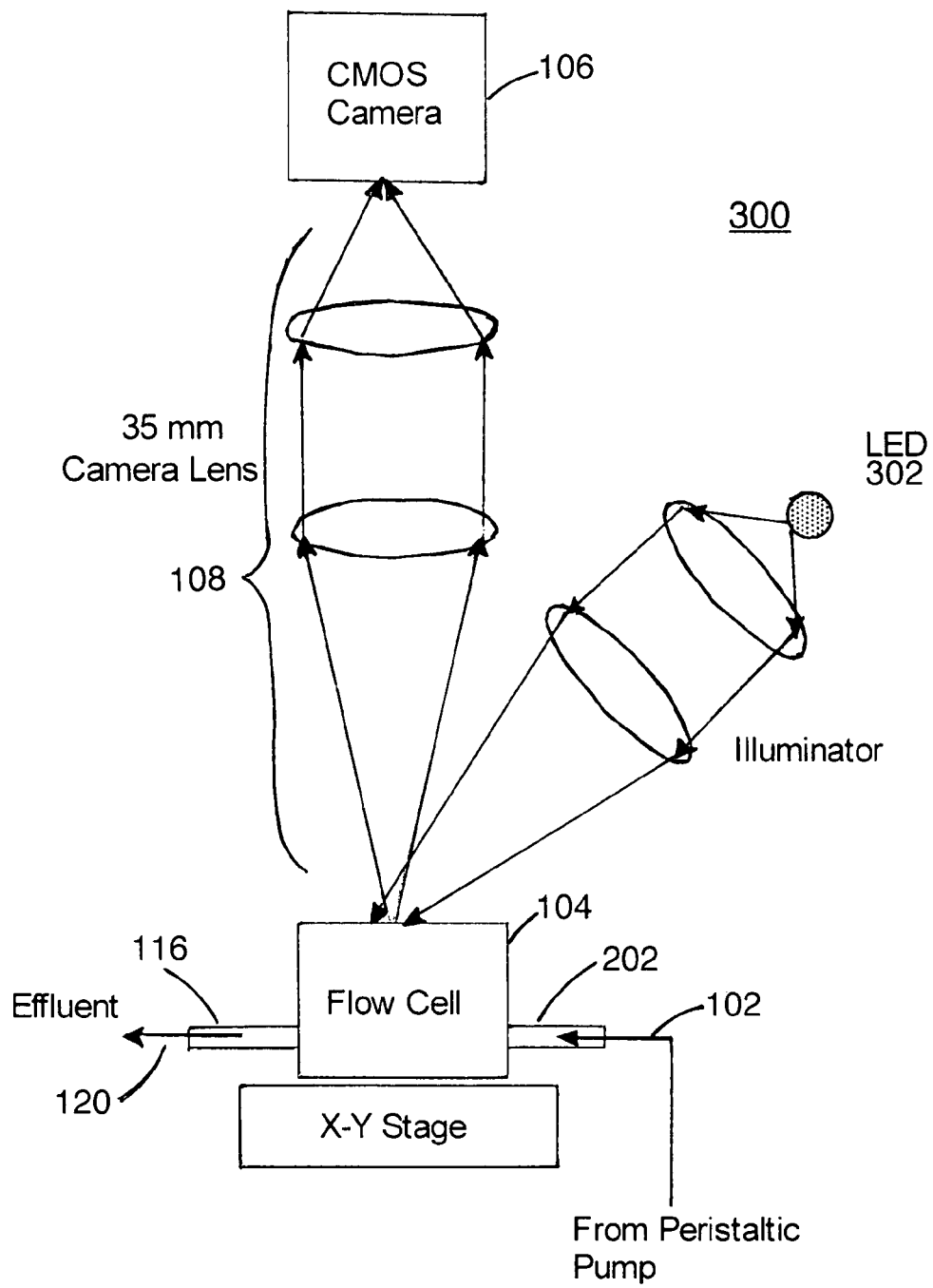
FIG. 3 (Prior Art) shows an LED illuminated epifluorescent fountain flow cytometer.
Figure 4:
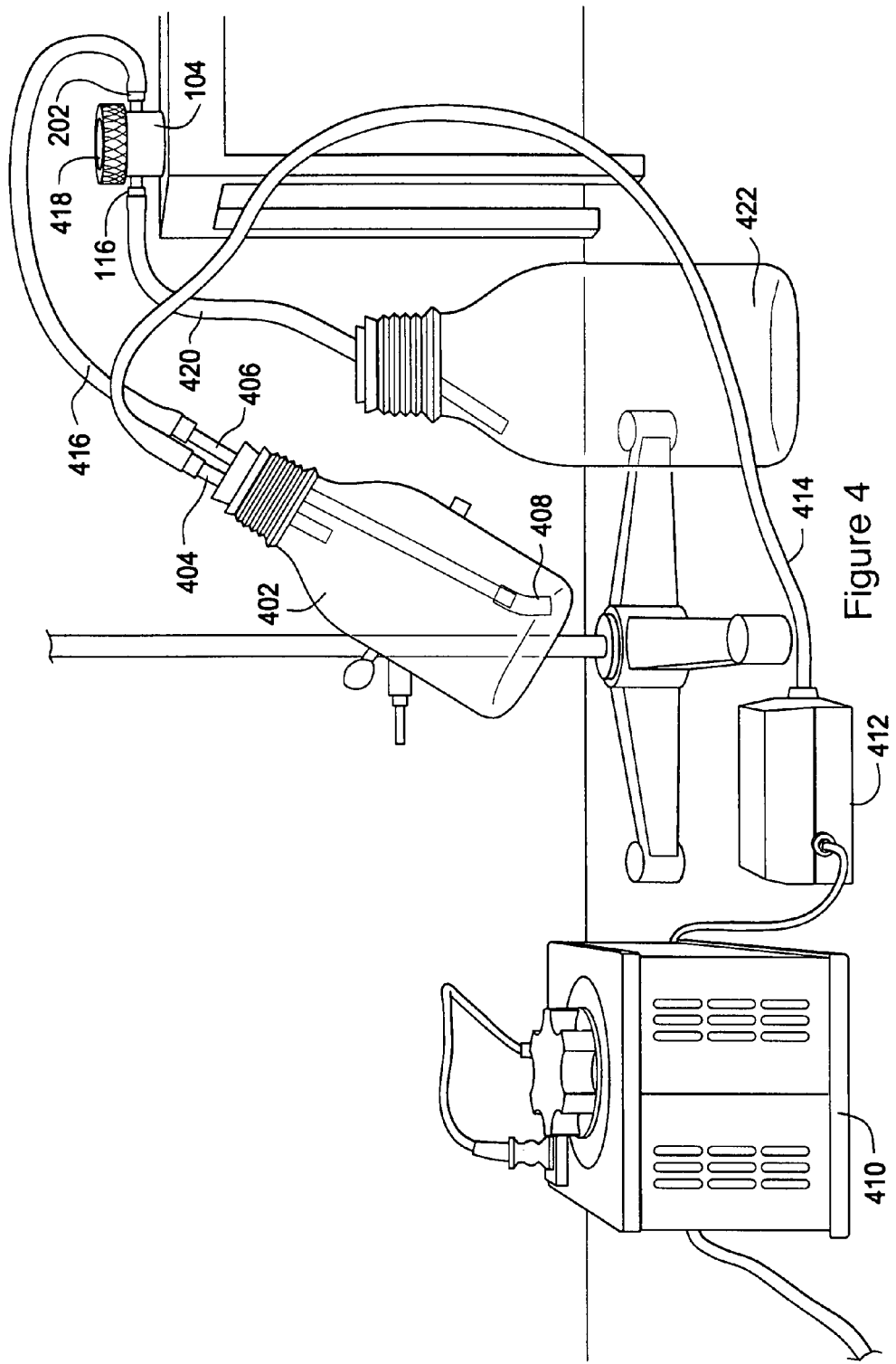
FIG. 4 is a schematic diagram showing a first preferred embodiment of a pumping system of the present invention.

FIG. 4 is a schematic diagram showing a first preferred embodiment of the pumping system of the present invention. A specific device is described below. The *Xenopus* pumping subsystem of FIG. 4 includes (left to right) a Variac (variable voltage transformer) 410, an aquarium air pump 412, a ring stand support for the sampling reservoir 402, a sampling reservoir 402, a flow cell 104, and a waste container 422. The sampling reservoir 402 is tilted by about 30 degrees, in order to gather the tadpoles at the bottom corner of the reservoir. The air pump 412 pumps air into a short stainless steel air pipe 404 via air tubing 414. The sample 102 is pumped from the lowest point in reservoir 402 through long stainless steel sample pipe 406/Tygon™ sample tubing 416 combination, to flow cell 104. From flow cell 104, the sample flows into waste container 422 via sample tubing 420.

In one embodiment, the reservoir 402 with *Xenopus* tadpoles is a 500 ml glass jar with a two-holed rubber stopper, with two 8-mm diameter stainless steel tubes inserted through the stopper. One of the pipes 404 is short, and is just long enough to extend through the stopper (FIGS. 4, 6A and 6B). The longer pipe 406 extends nearly to the bottom of the glass jar. At its lower end is preferably disposed a bent end piece 408 for better reaching the tadpoles. Air is pumped into the short pipe 404 via air tubing 414 with an inexpensive aquarium air pump 412, which runs on 120 Volts AC. The reservoir 402 is tilted, as the tadpoles prefer to settle at the lowest point. Air pressure from pump 412 causes the tadpoles to be pumped out of the reservoir, through flow cell 104, and into the glass "waste" container 422.

The flow rate is controlled with a variable transformer 410 (a "Variac"), but something more basic could be developed. (An air pump that runs with a DC power supply would work well.) The voltage is about 25 Volts AC to achieve a flow rate of about 140 ml/minute. Pumping more slowly than this results in the tadpoles not moving into the tubing.

Flow cell 104 could be the flow block shown in FIG. 4, having an entrance tube 202, a drain tube 116, and a viewing area 418. The rest of the measuring equipment is removed for clarity, but is shown in FIGS. 6A and 6B.

This system is superior to any system in which the tadpole goes through the pump, whether it is an impeller pump, diaphragm pump, piston pump, syringe pump, peristaltic pump, gear pump, or any other kind of mechanical pump. Mechanical pumps in general are not gentle with large, soft particles, such as tadpoles, flowing through them. Specifically, researchers have tried centrifugal/impeller pumps, and can't find a way to make them work without killing the tadpoles. The air pump system of FIG. 4 is very gentle with tadpoles; the same set of tadpoles can be pumped through the measuring device several times without killing them.

2. Analyzing and Sorting the Organisms

FIG. 5 is a block diagram illustrating a variation on the process performed by the present invention. The air pump 412 and sample reservoir 402 are shown in FIG. 4. An example of measuring equipment 508 is shown in FIGS. 6A and 6B. The result from the measuring step can be used to sort tadpoles according to fluorescence by triggering a valve 502 from the fluorescence measurement, which sorts the tadpoles into two or more bins 504, 506 according to fluorescent intensity.

FIG. 6A is schematic diagram of an embodiment of this invention showing sample reservoir 402 from FIG. 4 and FFC (Fountain Flow Cytometer) measuring equipment 508 with flow cell 104. Tadpoles are pumped into a fountain flow cytometer (FFC, U.S. Pat. No. 6,765,656; 2004) which measures the intensity of emission from the tadpole, excited with an LED 302. If the tadpoles are being measured for GFP expression, the FFC uses a blue LED with an excitation filter (not shown) for GFP, and the digital camera 106 uses an emission filter for GFP (not shown). The CMOS camera is used to continuously measure the emission from the flow cell 104, typically at a rate of 2-10 frames/second. A photometric measurement is made by summing the intensity of all of the pixels in the CMOS frame. (Alternatively, a photomultiplier tube or solid-state photodetector could be used to monitor the intensity.) Data is recorded as a time sequence of intensity measurements (similar to the output from a strip-chart recorder). Tadpole events appear as peaks in the data. A sample typically consists of 10-30 tadpoles in a 200-ml sample. The analysis results in a mean intensity and standard error, which is indicative of the level of pollutants in the sample for genetically modified *Xenopus*.

The measuring device is not limited to an FFC, but could be, for example, any system that measures the fluorescence of large particles in an aqueous sample.

FIG. 6B is a schematic diagram of the embodiment of FIG. 6A with the sample reservoir 402 outfitted with a "sample introduction unit" (shown as a funnel 606 in this case) to introduce a sample containing tadpoles into the sample reservoir 402. The unit has a sample introduction valve 604 that can be opened one way to allow tadpoles to be introduced into the sample reservoir 402 and another way to allow air 602 to be pumped into the sample reservoir 402 while keeping air from leaking through the sample introduction unit/chamber.

FIGS. 7A-7C illustrate several possible reservoir configurations for use with the present invention. These sample reservoirs accommodate organisms settling to the lowest point in the container. FIG. 7A is a tilted reservoir 702 including a bent pipe 708 to reach into its lowest corner. FIG. 7B is a dimpled reservoir 704. FIG. 7C is a tapered reservoir 706. Many *Xenopus* tadpoles tend to settle to the lowest point in the sample reservoir. It is expeditious to narrow or taper the bottom of the sample container so that as tadpoles settle to the bottom of the container, they settle near the input end of the long tube. This makes it easier for them to become swept up in the flow into the long tube. It is also possible to increase the velocity at the end of the long tube by narrowing its diameter at the end with a taper (not shown).

Figure 8:
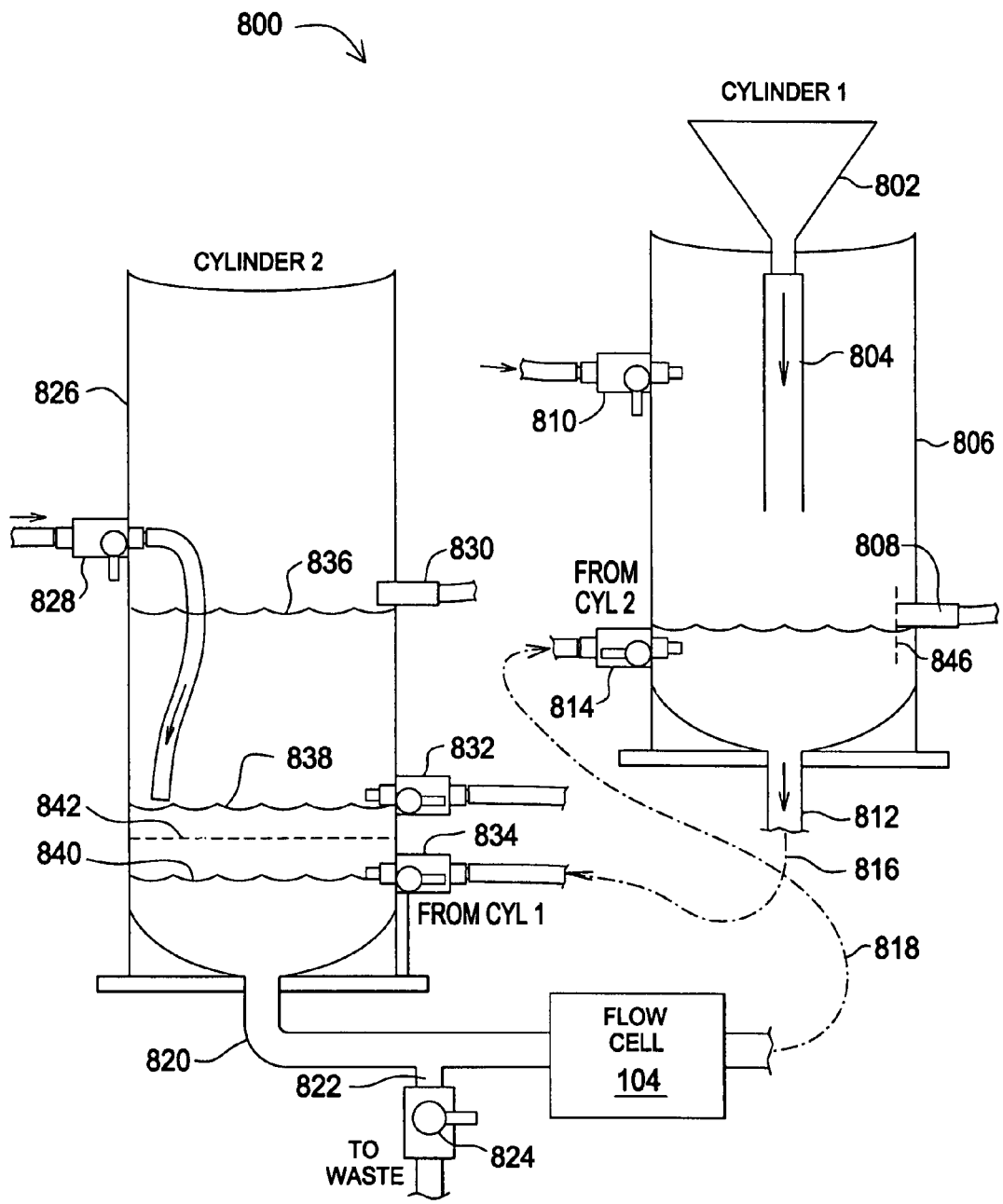
FIG. 8 is a schematic diagram illustrating a second preferred embodiment of a pumping system of the present invention.

FIG. 8 is a schematic diagram illustrating a second embodiment of a pumping device 800 according to the present invention. The embodiment of FIG. 8, called the Recirculating Tadpole Pump (RTP 800) uses only gravity to pump the tadpoles, and includes a method for measuring the same sample 102 several times. In this embodiment, the "sample reservoir" analog is Cylinder 2, and the "waste container" analog is Cylinder 1, except that since the sample can be recycled back to Cylinder 2 for repeated measurements, the sample in Cylinder 1 is not necessary waste.

RTP (800) is a gravity fed pumping system designed to pump a fixed sample 102 (typically 0.5 to 1.0 liter with ~40 tadpoles, ~4 mm in width) through a flow cell 104 to measure tadpole fluorescence for each of the tadpoles. During measurement, tadpoles are pumped from through the flow cell from Cylinder 2 (826), using the difference in fluid height between higher level 836 in Cylinder 2 and the fluid height in Cylinder 1 (806).

Tadpoles are sent back from Cylinder 1 to Cylinder 2 (either after initial introduction, or after each measurement), following path 816 via drain 812, by using the difference in water height between the fluid height in Cylinder 1 and lower fluid height level 838 in Cylinder 2.

The bottoms of the Cylinders 806, 826 are tapered to encourage tadpoles to flow into the outlets in the respective bases. In addition, washing/stirring water is piped into valves 810, 828 to introduce circulation into the cylinder from which the tadpoles are flowing, in order to overcome their natural inclination to remain at the walls of the cylinder. Wash water can also be used to flush any tadpoles remaining in the cylinder after it empties. The speed of the pump is preferably maintained at greater than about 150 ml/min to overcome the natural inclination of tadpoles to swim against the flow.

"Levelers" 808, 830, and 832 are openings in the cylinders that "when open" impose an upper limit on the fluid level in their respective cylinder. Levelers 830 and 808 are level maintaining outflows and do not require valves, as the water level should never be above their heights. The screen 846 at the mouth of leveler 808 keeps tadpoles from exiting the system at that point. Leveler 832 is a level maintaining valve and is used to reduce the fluid level in Cylinder 2 to level 838 when it is time to return the sample to Cylinder 2. A screen is not required, because screen 842, extending across Cylinder 2, keeps the tadpoles under it, and hence away from leveler 832. Furthermore, screen 842 is used to keep the sample volume 840 containing the tadpoles small, so that they are near drain 820 and will be readily swept by the flow into flow cell 104.

At the end of experiment, sample 102 can be removed from system 800 by using drain valve 824 to divert the sample from Cylinder 2 down drain tube 822 instead of into flow cell 104. An aquarium pump (not shown) may be used to pump water into the system, both to raise the fluid level in Cylinder 2 to level 836 to provide gravity pressure to pump sample through the flow cell 104, and for washing/stirring/filling.

A measurement cycle is described in detail below:
1. A sample 804 is introduced into Cylinder 1 (806) for example by hand through introduction funnel 802.
2. Valve 834 is opened, introducing the sample into Cylinder 2 (826), below screen 842. Leveler valve 832 has held the water level to lower level 838, below the water level in Cylinder 1, to maintain flow from Cylinder 1 to Cylinder 2. Leveler valve 832 may be left open during this step to keep the fluid level in Cylinder 2 low enough. The tadpoles are kept in Cylinder 2 by screen 842. A small amount of wash water is applied via valve 810 to flush any remaining samples in Cylinder 1.
3. Valves 832 and 834 are closed.
4. Cylinder 2 is filled with water by opening wash/stir/fill water valve 828 and pumping water into Cylinder 2 (pump not shown). Once the fluid level in Cylinder 2 reaches level 836, valve 814 is opened to begin measurements and the sample flows through flow cell 104 and follows path 818 from the flow cell to Cylinder 1. Upper level maintaining outflow 830 maintains the head at a constant level 836 to maintain a constant flow velocity through flow cell 104.
5. Pumping continues until all of the tadpoles have exited the container.
6. Tadpoles are now in Cylinder 1 and are ready for reintroduction to Cylinder A by returning to step 1.

All of the valves are currently manually operated, but can easily be operated by computer.

What is claimed is:

1. Apparatus for pumping a fluid sample containing multicellular organisms from a sample reservoir through a fluorescence-measuring device to a waste container without passing the organisms through a pump, the apparatus comprising:
   a sample reservoir containing the sample;
   apparatus for selectively applying a pressure differential between the sample reservoir and the waste container using gravity by raising the fluid level in the sample reservoir to a first level, the first level higher than the fluid level in the waste container;
a first outlet for connecting the sample reservoir to a fluorescence measuring device;
a waste container; and
a second outlet for connecting the fluorescence measuring device to the waste container;
wherein when the pressure differential is applied, a portion of the sample flows from the sample reservoir, through the first outlet, through the fluorescence measuring device, and through the second outlet to the waste container; and
wherein the portion of the sample does not pass through a pump.

2. The apparatus of claim 1 wherein the multi-cellular organisms are from 0.1 mm to 3 cm long.

3. The apparatus of claim 2 wherein the multi-cellular organisms are *Xenopus* tadpoles.

4. The apparatus of claim 1, further comprising means for passing the sample portion back from the waste container to the sample reservoir, comprising means for lowering the fluid level in the sample reservoir to a second level, the second level below the fluid level in the waste container, and a valve for allowing the sample portion to flow from the waste container to the sample reservoir.

5. The apparatus of claim 4 further including a screen in the sample reservoir configured to contain the organisms below the second level.

6. Apparatus for pumping a fluid sample containing multi-cellular organisms from a sample reservoir through a fluorescence-measuring device to a waste container without passing the organisms through a pump, the apparatus comprising:
a sample reservoir containing the sample, the sample reservoir configured to have a low area narrower than the sample reservoir cross-section into which the organisms can settle;
means for selectively applying a pressure differential between the sample reservoir and the waste container;
a first outlet for connecting the sample reservoir to a fluorescence measuring device;
a waste container; and
a second outlet for connecting the fluorescence measuring device to the waste container;
wherein when the pressure differential is applied, a portion of the sample flows from the sample reservoir, through the first outlet, through the fluorescence measuring device, and through the second outlet to the waste container; and
wherein the portion of the sample does not pass through a pump.

7. The apparatus of claim 6 wherein the first outlet includes a pipe extending into the low area to siphon the organisms.

8. The apparatus of claim 7, wherein the pipe includes an end bent to extend into the low area.

9. The apparatus of claim 1, wherein the pressure differential is sufficient to achieve a sample flow rate of about 140 ml/minute.

10. The apparatus of claim 1, wherein the fluorescent measuring device includes a detection element for measuring light intensity within the sample; and further comprising a mechanism for sorting organisms according to the measured light intensity after they exit the fluorescent measuring device.

11. The method of measuring fluorescence of multi-cellular organisms comprising the steps of:
placing a fluid sample containing the organisms within a sample reservoir;
providing a waste container;
placing a fluorescence measuring device in flow connection between the sample reservoir and the waste container;
selectively applying a pressure differential between the sample reservoir and the waste container by raising the fluid level in the sample reservoir higher than the fluid level in the waste container such that a portion of the sample flows from the sample reservoir through the fluorescence measuring device and into the waste container; and
the method not including the step of passing the portion of the sample through a pump.

12. The method of claim 11 wherein the step of applying pressure differential comprises the step of pumping air into the sample reservoir.

13. The method of claim 11, further including the step of transferring the sample back to the sample reservoir by lowering the fluid level within the sample reservoir below the fluid level within the waste container.

14. The method of claim 11 wherein the organisms are *Xenopus* tadpoles.

15. The method of claim 11, further including the steps of detecting light within the sample in the fluorescence-measuring device and sorting organisms according to detected light.

16. The apparatus of claim 6 wherein the sample reservoir has bottom surface comprising a generally flat, horizontal area and a concave area extending lower than the horizontal area.

17. The apparatus of claim 6 wherein the sample reservoir includes a bottom surface having a generally elliptical concave cross-section.

* * * * *